United States Patent [19]

Geroc

[11] 4,294,255
[45] Oct. 13, 1981

[54] INTRALUMINAL ANASTOMOSIS

[76] Inventor: Andre Geroc, 1823 Lee Rd., Cleveland Heights, Ohio 44118

[21] Appl. No.: 106,926

[22] Filed: Feb. 19, 1980

Related U.S. Application Data

[63] Continuation of Ser. No. 890,914, Apr. 17, 1978, abandoned.

[51] Int. Cl.³ .............................................. A61B 17/04
[52] U.S. Cl. ................................................ 128/334 C
[58] Field of Search ..................... 128/305, 334 C, 346

[56] References Cited

U.S. PATENT DOCUMENTS

| | | | |
|---|---|---|---|
| 2,638,901 | 5/1953 | Sugarbaker | 128/334 C |
| 3,147,754 | 9/1964 | Koessler | 128/346 |
| 3,155,095 | 11/1964 | Brown | 128/334 C |
| 3,166,072 | 1/1965 | Sullivan | 128/334 C |
| 3,254,651 | 6/1966 | Collito | 128/334 C |
| 3,258,012 | 6/1966 | Nakayama et al. | 128/334 C |
| 3,606,888 | 9/1971 | Wilkinson | 128/334 C |
| 3,774,615 | 11/1973 | Lim et al. | 128/334 C |
| 4,055,186 | 10/1977 | Leveen | 128/334 C |
| 4,206,757 | 6/1980 | Grandadam et al. | 128/260 |

FOREIGN PATENT DOCUMENTS 2657255  6/1978  Fed. Rep. of Germany ... 128/334 C

Primary Examiner—C. Fred Rosenbaum
Attorney, Agent, or Firm—Burge & Porter Co.

[57] ABSTRACT

Intraluminal anastomosis devices include complementary, ring-shaped clamping and pinning members for intraluminal end-to-end anastomosis of a tubular organ. The confronting faces of the devices have an annular, sharpened rim located at a radially innermost position. The confronting faces of the devices also include an annular groove located radially outwardly of the rim, the groove including a plurality of spaced, longitudinally extending openings having radially inwardly projecting serrations. Toothed pins are retained in the openings to securely clamp the devices and intervening tissue together.

7 Claims, 2 Drawing Figures

INTRALUMINAL ANASTOMOSIS

This application is a continuation of application Ser. No. 890,914 filed Apr. 17, 1978 and now abandoned.

BACKGROUND OF THE INVENTION

1. Field of the Invention

The invention relates to the field of surgery, more specifically, to intraluminal reunion of two disconnected parts of a tubular organ such as the bowel.

2. Description of the Prior Art

An intensive search has been made for a secure, standardized, easy to use, easy to detect postsurgically, simple and inexpensive anastomosis device; but the devices proposed in the past have not provided the desired solution. Leveen's anastomosis button, U.S. Pat. No. 4,055,186, undesirably significantly reduces the lumen of the bowel and the inverted ends of the bowel are not secured properly. Sullivan's barbed clips, U.S. Pat. No. 3,166,072, as well as Collito's discs and sleeves, U.S. Pat. No. 3,254,651, have not been accepted. Sugarbaker's surgical clamp, U.S. Pat. No. 2,638,901, is limited to recto-colic anastomosis only. None of the known prior devices function to properly grip the inverted ends of the organ so that shifting is not possible while at the same time providing a controlled flow of blood to the region where healing must occur.

SUMMARY OF THE INVENTION

In contrast to the aforementioned anastomosis devices, intraluminal anastomosis devices according to the invention do not impede the inner passage of the reunited bowel. The cut ends are secured against shifting by toothed protrusions and by a crest-like prominence without interrupting the blood supply in the reunited healing area. The devices are easily detectable postsurgically and the insertion procedure is so simple that one without any special skill can accomplish standard and reliable reunion of an intestine within one or two minutes. This markedly reduces the total operating time, reduces the amount of anesthetic, and contributes to sooner and better postsurgical recovery.

The advantages and features of the invention will become more readily apparent upon consideration of the following detailed description of the invention, taken in conjunction with the accompanying drawings.

DESCRIPTION OF THE PREFERRED EMBODIMENT

Figures 1, 2:
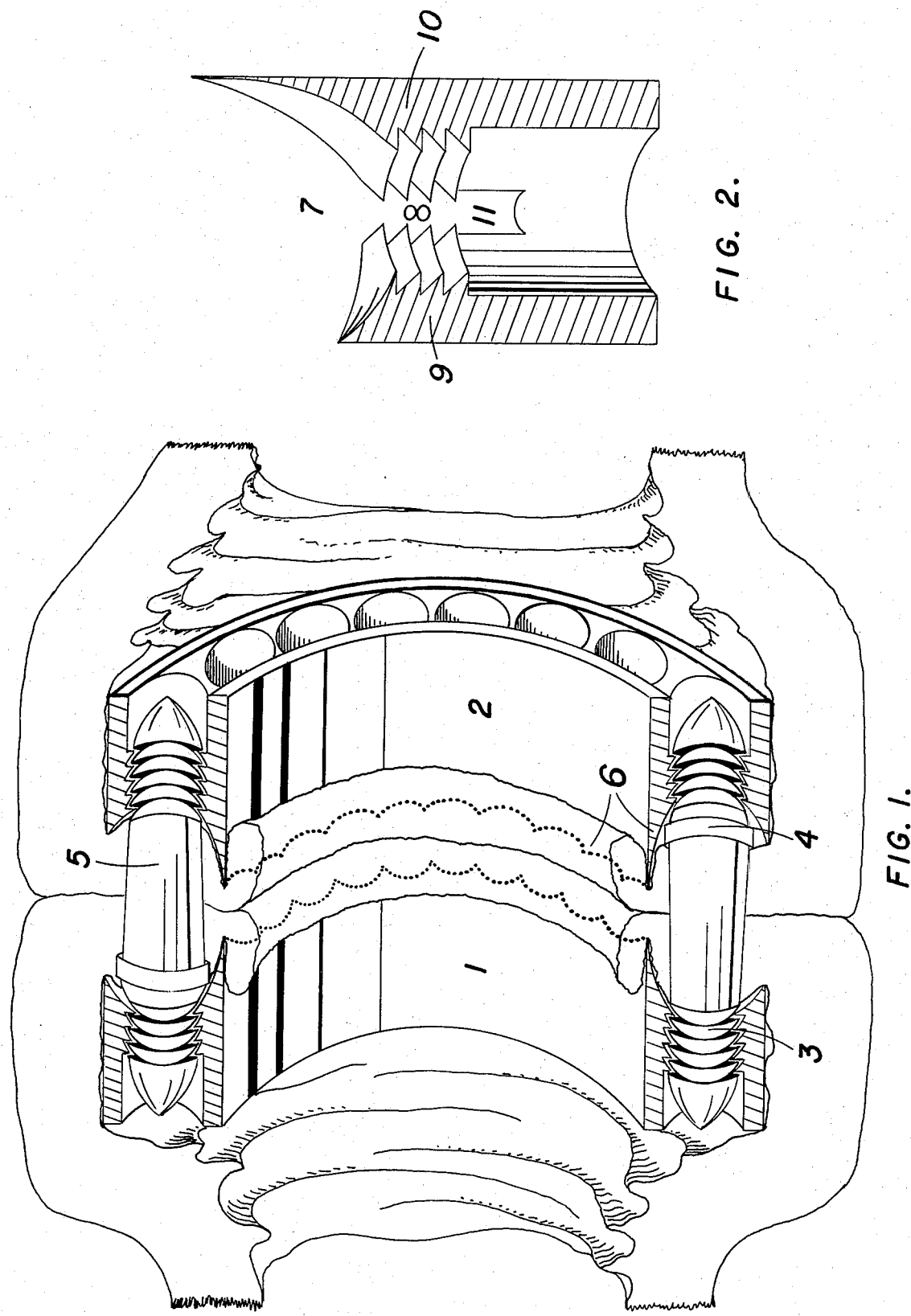
FIG. 1 is a schematic cross-sectional view of intraluminal end-to-end anastomosis of a tubular organ accomplished by a pair of intraluminal anastamosis devices according to the invention.
FIG. 2 is an enlarged view of a portion of one of the devices shown in FIG. 1.

Referring to FIGS. 1 and 2, intraluminal anastomosis devices 1 and 2 according to the invention are employed to clamp the cut, opposed ends of a tubular organ such as the bowel between them. The devices 1, 2 are complementary, ring-shaped members locked together by pins 5 having at their ends serrations 3. The central portion of each pin 5 is conical, and a ridge, or girdle 4 encircles the conical portion at the interface between the conical portion and one group of serrations 3. As can be seen in FIG. 1, the pins 5 extend between the inverted cut ends of the bowel. The cut ends are secured against leakage, shifting, or displacement by clamping with a sharpened rim, or crest-like prominence 6. As can be seen in FIG. 1, the rim 6 is scalloped at its edges and is located at the radially innermost portion of the devices 1, 2. The rim 6 extends outwardly of a radially innermost body portion 10. A second rim smaller than the rim 6 extends outwardly of a second, radially outermost body portion 9.

Referring particularly to FIG. 2, each device 1, 2 is provided with a plurality of longitudinally extending openings 7 located radially outwardly of the rim 6. The openings 7 are formed at the bottom of a grooveshaped margin located radially outwardly of the rim 6. Each of the openings 7 includes a plurality of radially inwardly extending serrations 8. The serrations engage the serrated portions 3 of the pins 5 so as to tightly, and irreversibly, lock the devices 1, 2 together.

In order to insure a positive engagement of the serrations 3 with the serrations 8, the pins 5 must be tightly fitted within the openings 7. The devices 1, 2 are provided with a circumferential channel 11 formed at the rearwardmost portion of the groove. Due to the tight fit of the pins 5 within the openings 7 and due to the flexibility provided by the channel 11, the body portion 9 and the body portion 10 are flexed apart upon insertion of the pins 5. As can be seen in FIG. 1, adjacent pins 5 face in opposite directions. Accordingly, the ridges 4 engage the entrance to the openings 7 to control the depth to which one end of the pins 5 extends within the openings 7.

As will be appreciated from an examination of FIGS. 1 and 2, the rim 6 extends a considerable distance outwardly from the body portion 10 of each device 1, 2. Together, the rim 6 and the smaller rim define the groove therebetween. The groove is somewhat recessed with respect to the portions 9, 10 so as to provide a place for tissue to be displaced. The second rim extends only slightly outwardly of the body portion 9 so as to provide a gentle clamping action for joined tissue.

The intraluminal anastomosis devices 1, 2 can be used for reunion of any tubular organ covered by serosa, but particularly the bowel. The number of implanted toothed pins 5 used with each of the two complementary devices 1, 2 may vary from three to four or more, depending on the decision of the surgeon. The devices 1, 2 are inserted in the lumen of a bowel by first inserting toothed pins 5 in alternating openings 7 until the ridges 4 engage the entrance to the openings 7. The cut ends of the bowel are inverted, pinned with the toothed pins 5, and mated together within a very short period of time.

Because the rims 6 extend furthest toward each other from the confronting faces of the devices 1, 2, the inverted ends of the tubular organ are securely clamped so that relative movement between the clamped ends is not possible. Eventually due to the tight clamping action, the tightly clamped portion of the bowel will undergo necrosis. Because the groove essentially provides a relieved region for the reception of tissue, blood flow to the region intermediate the grooves still will occur, thereby promoting healing of the joined tissue. The clamping action of the second rim is less than that of the rim 6, so that blood flow is not impeded, but some protection against leakage and shifting occurs. The effective width of the healing region as defined by the radial spacing between the rim 6 and the second rim is far greater than in prior devices. The extreme clamping action of the rims 6, combined with the great healing area provided by the grooves and the lesser clamping action of the second rims, provides an exceedingly effective intraluminal anastomosis technique compared with known prior techniques.

It will be appreciated that various modifications of the invention are possible within the scope of the invention as hereinafter claimed. It is intended that the appended claims shall cover whatever features of patentable novelty exist in the patent disclosed.

I claim:

1. Anastomosis devices for intraluminal, end-to-end connection of the severed ends of an intestine or other tubular organ, the devices including a pair of mating, ring-shaped, clamping members, each of the members comprising:
    (a) a circumferential, laterally extending, sharpened rim, the rim being located adjacent a radially innermost portion of the member;
    (b) a second, laterally extending rim, the second rim extending outwardly of the member on the same side as the sharpened rim but to a lesser extent than the sharpened rim, the second rim being located adjacent a radially outermost portion of the member;
    (c) a groove located intermediate the sharpened rim and the second rim; and
    (d) means for connecting the members together, the connecting means being in the region of the groove.

2. The anastomosis devices of claim 1, wherein the sharpened rim is scalloped at its edge.

3. The anastomosis devices of claim 1, wherein the connecting means includes toothed protrusions engageable with each of the clamping members, the toothed protrusions penetrating the ends of the organ to be joined and locking the members tightly together with the ends of the organ clamped therebetween.

4. The anastomosis devices of claim 3, wherein:
    (a) each of the grooves includes a plurality of longitudinally extending openings, the openings including serrations; and
    (b) the toothed protrusions are in the form of pins having serrations at each end, the serrations being engageable with the serrations included as part of the openings in the grooves.

5. The anastomosis devices of claim 4, further including a circumferential channel formed at the base of each of the grooves, the channel permitting the openings to be flexed apart upon insertion of the pins, whereby the pins are tightly fitted within the openings.

6. Anastomosis devices for intraluminal, end-to-end connection of the severed ends of an intestine or other tubular organ, wherein a pair of ring-shaped, clamping members compress the ends of the reunited organ between them and secure the ends from leakage, shifting, or displacement while at the same time assuring a proper supply of blood to the joined area, the devices comprising:
    (a) a sharpened, scalloped rim extending laterally outwardly of each device, the rim extending from a location adjacent a radially innermost portion of each device;
    (b) a second rim extending laterally outwardly of each device on the same side of the device as the sharpened rim, the second rim extending laterally outwardly a lesser distance than the sharpened rim;
    (c) a circumferential groove located intermediate the sharpened rim and the second rim;
    (d) toothed protrusions for joining the paired devices, the toothed protrusions including a plurality of pins having serrations at their ends, the pins penetrating the inverted ends of the organ to be joined; and
    (e) a plurality of laterally extending openings included as part of each of the grooves, the openings being spaced circumferentially about the devices and including serrations engageable with the serrations of the pins so as to lock the devices tightly together with the ends of the organ clamped therebetween.

7. The anastomosis devices of claim 6, further comprising a circumferential channel formed at the base of each of the grooves, the channel permitting the openings to be flexed apart upon insertion of the pins, whereby the pins will be tightly fitted within the openings.

* * * * *